(12) United States Patent
Zagar et al.

(10) Patent No.: US 10,512,266 B2
(45) Date of Patent: Dec. 24, 2019

(54) HERBICIDAL COMPOSITIONS BASED ON 3-PHENYLURACILS AND N-[[4-[CYCLOPROPYLAMINO)-CARBONYL]PHENYL]SULFONYL]-2-METHOXYBENZAMIDE

(75) Inventors: Cyrill Zagar, Hong Kong (CN); Bernd Sievernich, Haßloch (DE)

(73) Assignee: BASF SE, Ludwigshafen (DE)

( * ) Notice: Subject to any disclaimer, the term of this patent is extended or adjusted under 35 U.S.C. 154(b) by 1800 days.

(21) Appl. No.: 12/089,800

(22) PCT Filed: Oct. 5, 2006

(86) PCT No.: PCT/EP2006/067061
§ 371 (c)(1),
(2), (4) Date: May 2, 2008

(87) PCT Pub. No.: WO2007/042447
PCT Pub. Date: Apr. 19, 2007

(65) Prior Publication Data
US 2008/0254985 A1 Oct. 16, 2008

(30) Foreign Application Priority Data
Oct. 12, 2005 (EP) .................................... 05022222

(51) Int. Cl.
*A01N 43/54* (2006.01)
(52) U.S. Cl.
CPC .................................... *A01N 43/54* (2013.01)
(58) Field of Classification Search
CPC ..... A01N 43/54; A01N 2300/00; A01N 25/32
See application file for complete search history.

(56) References Cited

U.S. PATENT DOCUMENTS

| | | | |
|---|---|---|---|
| 6,251,827 B1 | 6/2001 | Ziemer et al. | |
| 6,376,429 B1 | 4/2002 | Van Almsick et al. | |
| 2004/0087445 A1 | 5/2004 | Ziemer et al. | |
| 2007/0066481 A1 | 3/2007 | Ziemer et al. | |

FOREIGN PATENT DOCUMENTS

| | | | |
|---|---|---|---|
| CA | 2378840 | 2/2001 | |
| DE | 19846792 | 4/2000 | |
| EP | 338 992 | 10/1989 | |
| WO | WO 99/16744 | 4/1999 | |
| WO | WO 00/15615 | 3/2000 | |
| WO | WO 01/08487 | 2/2001 | |
| WO | WO 01/83459 | 11/2001 | |
| WO | WO 02/36595 | 5/2002 | |
| WO | WO 03/24221 | 3/2003 | |
| WO | WO 04/021788 | 3/2004 | |
| WO | WO 04/80183 | 11/2004 | |
| WO | WO 05/00797 | 1/2005 | |
| WO | WO 06/61562 | 6/2006 | |
| WO | WO2011/064533 | * 6/2011 | ............. A01N 43/54 |

OTHER PUBLICATIONS

International Preliminary Report on Patentability and Written Opinion of the International Searching Authority for International Application No. PCT/EP2006/067061, International Filing Date of May 10, 2006.
International Search Report (WO 2007/042447 A3) for International Application No. PCT/EP2006/067061.
Abu-Qare, Aqel W., et al. "Herbicide safeners: uses, limitations, metabolism, and mechanisms of action", Chemosphere, 2002, p. 965-974, vol. 48.
Davies, Joanna, "Herbicide Safeners—Commercial Products and Tools for Agrochemical Research", Pesticide Outlook from the Royal Society of Chemistry, 2001, pp. 9-15.

* cited by examiner

*Primary Examiner* — Johann R Richter
*Assistant Examiner* — Danielle Sullivan
(74) *Attorney, Agent, or Firm* — Brinks Gilson & Lione

(57) ABSTRACT

The present invention is related to compositions comprising 3-phenyluracils I, wherein the variables R1 to R7 are as defined in the specification, including their agriculturally acceptable salts; and N-[[4-[(cyclopropylamino)carbonyl]phenyl]sulfonyl]-2-methoxy-benzamide II including its agriculturally acceptable salts; and optionally at least one herbicide III selected from the classes III.1) to III.15) defined as in the specification including their agriculturally acceptable salts and, provided they have a carboxyl group, their agriculturally acceptable derivatives.

11 Claims, No Drawings

HERBICIDAL COMPOSITIONS BASED ON 3-PHENYLURACILS AND N-[[4-[CYCLOPROPYLAMINO)-CARBONYL]PHENYL]SULFONYL]-2-METHOXYBENZAMIDE

This application is a National Stage application of International Application No. PCT/EP2006/067061 filed Oct. 5, 2006, the entire contents of which is hereby incorporated herein by reference. This application also claims the benefit under 35 U.S.C. § 119 of European Patent Application No. 05022222.3, filed Oct. 12, 2005, the entire contents of which is hereby incorporated herein by reference.

The present invention relates to herbicidally active compositions comprising 3-phenyluracils I, N-[[4-[(cyclopropylamino)carbonyl]phenyl]sulfonyl]-2-methoxybenzamide II and optionally at least one further herbicide III.

In crop protection products, it is desirable in principle to increase the specificity and the reliability of the action of active compounds. In particular, it is desirable for the crop protection product to control the harmful plants effectively and, at the same time, to be tolerated by the useful plants in question. It is known that in some cases better crop plant compatibility can be achieved by joint application of specifically acting herbicides with organic active compounds, which act as antidotes or antagonists. Owing to the fact that they can reduce or even prevent damage to the crop plants, they are also referred to as safeners.

3-phenyluracils I and compositions comprising 3-phenyluracils I are known as highly effective herbicides (e.g. WO 01/83459, WO 03/24221, WO 04/80183). However, their compatibility with dicotyledonous crop plants such as cotton, oilseed rape, flax, lentil, sugar beet, tobacco, sunflowers and soybeans and some gramineaceous plants such as oat, barley, millet, corn, rice, wheat and sugar cane is not always satisfactory, i.e. in addition to the harmful plants, the crop plants are also damaged to an extent which is not acceptable. It is possible to spare the useful plants by lowering the application rates; however the extent of the control of harmful plants is naturally also reduced.

Therefore it is an object of the present invention to improve the crop-plant compatibility of 3-phenyluracils I, optionally in the presence of further herbicides II.

Surprisingly it has now been found that compositions comprising at least one 3-phenyluracil I or its agriculturally acceptable salts, N-[[4-[(cyclopropylamino)carbonyl]-phenyl]sulfonyl]-2-methoxybenzamide II or its agriculturally acceptable salts; and optionally at least one further herbicide III, improve the crop-plant compatibility of 3-phenyluracils I.

N-[[4-[(cyclopropylamino)carbonyl]phenyl]sulfonyl]-2-methoxybenzamide II (CAS no. 221667-31-8)

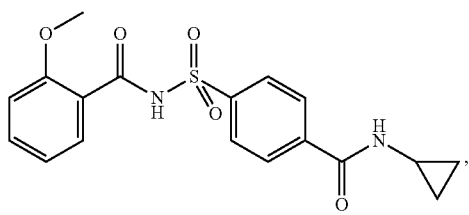

is a safener, which is disclosed, for example, in WO 99/16744 and WO 05/00797.

The herbicides III of groups III.1) to III.15) are known herbicides, see the quoted literature references and, for example, The Compendium of Pesticide Common Names ; Farm Chemicals Handbook 2000, Vol. 86, Meister Publishing Company, 2000; B. Hock, C. Fedtke, R. R. Schmidt, Herbizide, Georg Thieme Verlag, Stuttgart 1995; W. H. Ahrens, Herbicide Handbook, 7th Edition, Weed Science Society of America, 1994; and K. K. Hatzios, Herbicide Handbook, Supplement to $7^{th}$ Edition, Weed Science Society of America, 1998.

The present invention is therefore related to compositions comprising 3-phenyluracils I

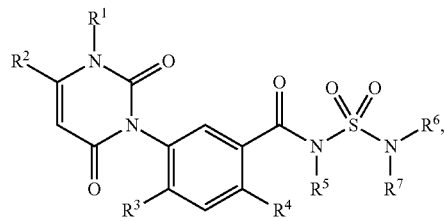

wherein the variables $R^1$ to $R^7$ are as defined below:
$R^1$ is methyl or $NH_2$;
$R^2$ is $C_1$-$C_2$-haloalkyl;
$R^3$ is hydrogen or halogen;
$R^4$ is halogen or cyano;
$R^5$ is hydrogen or $C_1$-$C_6$-alkyl;
$R^6$, $R^7$ independently of one another are hydrogen, $C_1$-$C_6$-alkyl, $C_1$-$C_6$-alkoxy, $C_3$-$C_6$-alkenyl, $C_3$-$C_6$-alkynyl, $C_3$-$C_7$-cycloalkyl, $C_3$-$C_7$-cycloalkenyl, phenyl or benzyl;
including their agriculturally acceptable salts; and
N-[[4-[(cyclopropylamino)carbonyl]phenyl]sulfonyl]-2-methoxybenzamide II

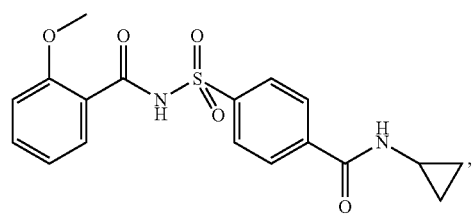

including its agriculturally acceptable salts;
and optionally at least one herbicide III selected from the following classes III.1) to III.15):
 III.1) lipid biosynthesis inhibitors;
 III.2) acetolactate synthase inhibitors (ALS inhibitors);
 III.3) photosynthesis inhibitors;
 III.4) protoporphyrinogen-IX oxidase inhibitors;
 III.5) bleacher herbicides;
 III.6) enolpyruvyl shikimate 3-phosphate synthase inhibitors (EPSP inhibitors);
 III.7) glutamine synthetase inhibitors;
 III.8) 7,8-dihydropteroate synthase inhibitors (DHP inhibitors);
 III.9) mitose inhibitors;
 III.10) inhibitors of the synthesis of long chain fatty acids (VLCFA inhibitors);
 III.11) cellulose biosynthesis inhibitors;
 III.12) decoupler herbicides;
 III.13) auxin herbicides;
 III.14) auxin transport inhibitors;

III.15) other herbicides selected from the group consisting of benzoylprop, flamprop, flamprop-M, bromobutide, chlorflurenol, cinmethylin, methyldymuron, etobenzanid, fosamine, metam, pyributicarb, oxaziclomefone, dazomet, triaziflam and methyl bromide;

including their agriculturally acceptable salts and, provided they have a carboxyl group, their agriculturally acceptable derivatives.

The invention relates in particular to compositions in the form of safened herbicidally active crop protection compositions comprising a herbicidally effective amount of at least one composition of 3-phenyluracil I with N-[[4-[(cyclopropylamino)carbonyl]-phenyl]sulfonyl]-2-methoxybenzamide II and optionally at least one herbicide III, as defined above, and at least one inert liquid and/or solid carrier, if desired at least one or more surfactants and, if appropriate, at least one or more further auxiliaries customary for crop protection compositions.

The invention also relates to compositions in the form of a crop protection composition formulated as a 2-component composition comprising a first component, which comprises the 3-phenyluracil I and the N-[[4-[(cyclopropyl-amino)carbonyl]phenyl]sulfonyl]-2-methoxybenzamide II, a solid or liquid carrier and, if appropriate, one or more surfactants, and a second component, which comprises at least one further herbicide III and optionally the N-[[4-[(cyclopropylamino)carbonyl]phenyl]sulfonyl]-2-methoxybenzamide II, a solid or liquid carrier and, if appropriate, one or more surfactants, where both components may additionally comprise further auxiliaries customary for crop protection compositions.

The invention also relates to compositions in the form of a crop protection composition formulated as a 2-component composition comprising a first component, which comprises the 3-phenyluracil I and optionally the N-[[4-[(cyclopropylamino)carbonyl]phenyl]sulfonyl]-2-methoxybenzamide II, a solid or liquid carrier and, if appropriate, one or more surfactants, and a second component, which comprises at least one further herbicide III and the N-[[4-[(cyclopropylamino)carbonyl]phenyl]sulfonyl]-2-methoxybenzamide II, a solid or liquid carrier and, if appropriate, one or more surfactants, where both components may additionally comprise further auxiliaries customary for crop protection compositions.

The invention furthermore relates to a method for controlling undesired vegetation, which comprises allowing a herbicidally effective amount of a composition according to the present invention to act on plants, their habitat or on seed.

The invention furthermore relates to a method for controlling undesired vegetation, which comprises applying a herbicidal composition according to the present invention before, during and/or after the emergence of the undesirable plants, the components I, II and optionally III being applied simultaneously or in succession.

The invention furthermore relates to a method for controlling undesirable vegetation in crops, in particular in crops of oat, barley, millet, corn, rice, wheat, sugar cane, cotton, oilseed rape, flax, lentil, sugar beet, tobacco, sunflowers and soybeans or in perennial crops.

The invention furthermore relates to a method for controlling undesirable vegetation in crops which, by genetic engineering or by breeding, are resistant to one or more herbicides and/or fungicides and/or or to attack by insects.

The invention furthermore relates to a method of safening the phytotoxic activity of a 3-phenyluracil I, or an agriculturally acceptable salt thereof, according to the present invention on crops;

preferably crops selected from oat, barley, millet, corn, rice, wheat, sugar cane, cotton, oilseed rape, flax, lentil, sugar beet, tobacco, sunflowers, soybeans, rye, triticale, potato, peas, beans, sorghum, grapes, citrus, apple and almond;

especially preferred crops selected from oat, barley, millet, corn, rice, wheat, sugar cane, cotton, oilseed rape, flax, lentil, sugar beet, tobacco, sunflowers and soybeans;

which comprises applying said 3-phenyluracil I, or an agriculturally acceptable salt thereof, in combination with N-[[4-[(cyclopropylamino)carbonyl]phenyl]sulfonyl]-2-methoxybenzamide of formula II or an agriculturally acceptable salt thereof; and optionally at least one herbicide III selected from the classes III.1) to III.15) as defined herein, in an amount effective to reduce or eliminate the phytotoxic activity of said 3-phenyluracil I.

In these methods it is immaterial whether the herbicide I, safener II and optionally III are formulated and applied jointly or separately, and, in the case of separate application, in which order the application takes place.

The organic moieties mentioned in the definition of the substituents $R^2$, $R^5$, $R^6$, $R^7$ in formula I are—like the term halogen—collective terms for individual enumerations of the individual group members. All hydrocarbon chains, i.e. all alkyl, haloalkyl, cycloalkyl, alkoxy, alkenyl, cycloalkenyl and alkynyl groups, can be straight-chain or branched, the prefix $C_n$-$C_m$ denoting in each case the possible number of carbon atoms in the group. Halogenated substituents preferably carry one, two, three, four or five identical or different halogen atoms. The term halogen denotes in each case fluorine, chlorine, bromine or iodine.

Examples of other meanings are:

$C_1$-$C_4$-alkyl: $CH_3$, $C_2H_5$, n-propyl, $CH(CH_3)_2$, n-butyl, $CH(CH_3)$—$C_2H_5$, $CH_2$—$CH(CH_3)_2$ and $C(CH_3)_3$;

$C_1$-$C_6$-alkyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$-$C_2$-haloalkyl: a methyl or ethyl radical, which is partially or fully substituted by fluorine, chlorine, bromine and/or iodine, for example $CH_2F$, $CHF_2$, $CF_3$, $CH_2Cl$, dichloromethyl, trichloromethyl, chlorofluoromethyl, dichlorofluoromethyl, chlorodifluoromethyl, 2-fluoroethyl, 2-chloroethyl, 2-brom-oethyl, 2-iodoethyl, 2,2-difluoroethyl, 2,2,2-trifluoroethyl, 2-chloro-2-fluor-oethyl, 2-chloro-2,2-difluoroethyl, 2,2-dichloro-2-fluoroethyl, 2,2,2-tri-chloroethyl, $C_2F_5$;

$C_1$-$C_4$-alkoxy: $OCH_3$, $OC_2H_5$, n-propoxy, $OCH(CH_3)_2$, n-butoxy, $OCH(CH_3)$—$C_2H_5$, $OCH_2$—$CH(CH_3)_2$ or $OC(CH_3)_3$, preferably $OCH_3$, $OC_2H_5$ or $OCH(CH_3)_2$;

$C_1$-$C_6$-alkoxy: a $C_1$-$C_4$-alkoxy radical as mentioned above, and also, for example pentoxy, 1-methylbutoxy, 2-methylbutoxy, 3-methoxylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-tri-methylpropoxy, 1,2,2-trimethylpropoxy, 1-ethyl-1-methylpropoxy and 1-ethyl-2-methylpropoxy;

$C_3$-$C_6$-alkenyl: prop-1-en-1-yl, allyl, 1-methylethenyl, 1-buten-1-yl, 1-buten-2-yl, 1-buten-3-yl, 2-buten-1-yl, 1-methylprop-1-en-1-yl, 2-methylprop-1-en-1-yl, 1-methylprop-2-en-1-yl, 2-methylprop-2-en-1-yl, n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methyl pent-2-en-1-yl, 2-methyl pent-2-en-1-yl, 3-methyl pent-2-en-1-yl, 4-methyl pent-2-en-1-yl, 1-methylpent-3-en-1-yl, 2-methyl pent-3-en-1-yl, 3-methyl pent-3-en-1-yl, 4-methyl pent-3-en-1-yl, 1-methyl pent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl or 1-ethyl-2-methylprop-2-en-1-yl;

$C_3$-$C_6$-alkynyl: prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methyl pent-1-yn-1-yl, 4-methyl pent-2-yn-4-yl or 4-methyl pent-2-yn-5-yl, preferably prop-2-yn-1-yl;

$C_3$-$C_7$-cycloalkyl: a monocyclic saturated hydrocarbon ring having 3 to 7 ring members, such as cyclopropyl, cyclobutyl, cyclopentyl, cyclohexyl or cycloheptyl;

$C_3$-$C_7$-cycloalkenyl: monocyclic unsaturated hydrocarbon ring having 3 to 7 ring members, such as cycloprop-1-enyl, cycloprop-2-enyl, cyclobut-1-enyl, cyclobut-2-enyl, cyclobut-1,3-dienyl, cyclopent-1-enyl, cyclopent-2-enyl, cyclopent-3-enyl, cyclopent-2,4-dienyl, cyclohex-1-enyl, cyclohex-2-enyl, cyclohex-3-enyl; cyclohex-1,3-dienyl, cyclohex-1,5-dienyl, cyclohex-2,4-dienyl, or cyclohex-2,5-dienyl.

If the phenyluracils I and/or the herbicides III are capable of forming geometrical isomers, for example E/Z isomers, it is possible to use both the pure isomers and compositions thereof in the compositions according to the invention. If the phenyluracils I and/or the herbicides III have one or more centers of chirality and, as a consequence, are present as enantiomers or diastereomers, it is possible to use both the pure enantiomers and diastereomers and their compositions in the compositions according to the invention.

If the phenyluracils and/or the herbicides III have functional groups, which can be ionized, they can also be used in the form of their agriculturally acceptable salts. Also, N-[[4-[(cyclopropylamino)carbonyl]phenyl]sulfonyl]-2-methoxybenzamide can be used in the form of its agriculturally acceptable salts. In general, the salts of those cations or anions are suitable whose cations or anions have no adverse effect on the action of the active compounds ("agricultural acceptable").

Preferred cations are the ions of the alkali metals, preferably of lithium, sodium and potassium, of the alkaline earth metals, preferably of calcium and magnesium, and of the transition metals, preferably of manganese, copper, zinc and iron, furthermore ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)eth-1-ylammonium, di(2-hydroxyeth-1-yl)ammonium, benzyltrimethylammonium, benzyltriethylammonium, furthermore phosphonium ions, sulfonium ions, preferably tri($C_1$-$C_4$-alkyl)sulfonium such as trimethylsulfonium, and sulfoxonium ions, preferably tri($C_1$-$C_4$-alkyl)sulfoxonium.

It is possible to use the phenyluracils of the formula I, the safener N-[[4-[(cyclopropylamino)carbonyl]phenyl]sulfonyl]-2-methoxybenzamide II, and optionally at least one herbicide III selected from chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, propaquizafop, quizalofop, quizalofop-P, trifop, alloxydim, butroxydim, clethodim, cloproxydim, cycloxydim, profoxydim, sethoxydim, tepraloxydim, tralkoxydim, amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, propoxycarbazon, flucarbazon, imazamethabenz, imazamox, imazapic, imazapyr, imazaquin, imazethapyr, cloransulam, diclosulam, florasulam, flumetsulam, metosulam, penoxsulam, bispyribac, pyrithiobac, flucetosulfuron, orthosulfamuron, pyrimisulfam, [N-(5,7-dimethoxy[1,2,4]triazolo[1,5-a]-pyrimidin-2-yl-2-methoxy-4-(trifluoromethyl)-3-pyridinsulfonamide, pyriminobac, bentazon, acifluorfen, ethoxyfen, fluoroglycofen, fomesafen, halosafen, lactofen, pyraflufen, flumiclorac, fluthiacet, carfentrazone, flufenpyr, mesotrione, sulcotrione, topramezone, 4-hydroxy-3-{[2-methyl-6-(trifluoromethyl)-3-pyridinyl]carbonyl}bicylo-[3.2.1]oct-3-en-2-one, 4-hydroxy-3-{2-(2-methoxyethoxy)methyl-6-(trifluoromethyl)-3-pyridinyl]carbonyl}bicyclo[3.2.1]oct-3-en-2-one, 4-hydroxy-3-[4-(methylsulfonyl)-2-nitrobenzoyl]-bicyclo[3.2.1]oct-3-en-2-one, 2-[2-chloro-4-(methylsulfonyl)-3-[(2,2,2-trifluoroethoxy)methyl] benzoyl]-3-hydroxy-2-cyclohexen-1-one, pyrasulfotole, glyphosate, glufosinate, bilanaphos, clomeprop, 2,4-D, 2,4-DB, dichlorprop, dichlorprop-P, MCPA, MCPB, mecoprop, mecoprop-P, 2,4,5-T, chloramben, dicamba, 2,3,6-TBA, tricamba, quinclorac, quinmerac, clopyralid, fluoroxypyr, picloram, triclopyr, aminopyralid, naptalam, diflufenzopyr, cloquintocet, fenchlorazole, isoxadifen and mefenpyr, in the form of salts with the agriculturally useful cations mentioned above.

Anions of useful acid addition salts are primarily chloride, bromide, fluoride, iodide, hydrogen sulfate, methyl sulfate, sulfate, dihydrogen phosphate, hydrogen phosphate, nitrate, dicarbonate, carbonate, hexafluorosilicate, hexafluorophosphate, benzoate and the anions of $C_1$-$C_4$-alkanoic acids, preferably formate, acetate, propionate and butyrate.

According to the invention, the herbicides cyperquat, diethamquat, difenzoquat, diquat, morfamquat and paraquat are usually employed in the form of salts with the agriculturally useful anions mentioned above.

According to the invention, the active compounds which carry a carboxyl group can, instead of the active compounds mentioned above, also be employed in the form of an agriculturally acceptable derivative, for example as amides such as mono- or di-$C_1$-$C_6$-alkylamides or arylamides, as esters, for example as allyl esters, propargyl esters, $C_1$-$C_{10}$-alkyl esters or alkoxyalkyl esters, and also as thioesters, for example as $C_1$-$C_{10}$-alkyl thioesters. Examples of active compounds having a COOH group which can also be employed as derivatives are: chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, propaquizafop, quizalofop, quizalofop-P, trifop, bensulfuron, chlorimuron, ethametsulfuron, flupyrsulfuron, halosulfuron, iodosulfuron, mesosulfuron, metsulfuron, primisulfuron, pyrazosulfuron, sulfometuron, thifensulfuron, tribenuron, triflusulfuron, imazamethabenz, imazamox, imazapic, imazapyr, imazaquin, imazethapyr, cloransulam, bispyribac, pyrithiobac, pyriminobac, acifluorfen, ethoxyfen, fluoroglycofen, lactofen, pyraflufen, flumiclorac, fluthiacet, carfentrazone, flufenpyr, clomeprop, 2,4-D, 2,4-DB, dichlorprop, dichlorprop-P, MCPA, MCPB, mecoprop, mecoprop-P, 2,4,5-T, chloramben, dicamba, 2,3,6-TBA, tricamba, quinclorac, quinmerac, clopyralid, fluoroxypyr, picloram, triclopyr, aminopyralid, naptalam, diflufenzopyr, cloquintocet, fenchlorazole, isoxadifen and mefenpyr. Preferred mono- and di-$C_1$-$C_6$-alkylamides are the methyl- and the dimethylamides. Preferred arylamides are, for example, the anilidines and the 2-chloroanilides. Preferred alkyl esters are, for example, the methyl, ethyl, propyl, isopropyl, butyl, isobutyl, pentyl, mexyl (1-methylhexyl) or isooctyl (2-ethylhexyl) esters. Preferred $C_1$-$C_4$-alkoxy-$C_1$-$C_4$-alkyl esters are the straight-chain or branched $C_1$-$C_4$-alkoxyethyl esters, for example the methoxyethyl, ethoxyethyl or butoxyethyl esters. An example of the straight-chain or branched $C_1$-$C_{10}$-alkyl thioesters is the ethyl thioester.

Among the 3-phenyluracils of formula I, preference is given to those wherein the variables $R^1$ to $R^7$ independently of one another, but preferably combined, have the meanings given below:
$R^1$ is methyl or $NH_2$;
$R^2$ is trifluoromethyl;
$R^3$ is hydrogen, fluorine or chlorine, in particular fluorine;
$R^4$ is halogen or cyano, in particular chlorine or cyano;
$R^5$ is hydrogen;
$R^6$, $R^7$ independently of one another are hydrogen, $C_1$-$C_6$-alkyl, $C_3$-$C_6$-alkenyl, $C_3$-$C_6$-alkynyl, $C_3$-$C_7$-cycloalkyl, $C_3$-$C_7$-cycloalkenyl, phenyl or benzyl;
in particular hydrogen or $C_1$-$C_6$-alkyl.

$R^6$ and $R^7$ are in particular identical or different $C_1$-$C_6$-alkyl radicals.

In a particularly preferred embodiment of the invention, the compositions comprise at least one 3-phenyluracil I in which the variables $R^1$ to $R^7$ in formula I have the following meanings (hereinbelow also referred to as 3-phenyluracils Ia):
$R^1$ is methyl;
$R^2$ is trifluoromethyl;
$R^3$ is fluorine;
$R^4$ is chlorine;
$R^5$ is hydrogen;
$R^6$, $R^7$ independently of one another are $C_1$-$C_6$-alkyl.

In another particularly preferred embodiment of the invention, the compositions comprise at least one 3-phenyluracil I in which the variables $R^1$ to $R^7$ in formula I have the meanings below (hereinbelow also referred to as 3-phenyluracils Ib):
$R^1$ is $NH_2$;
$R^2$ is trifluoromethyl;
$R^3$ is fluorine;
$R^4$ is chlorine;
$R^5$ is hydrogen;
$R^6$, $R^7$ independently of one another are $C_1$-$C_6$-alkyl.

Particularly preferred herbicides I are 3-phenyluracils I.1, especially preferred 3-phenyluracils I.1.1 to I.1.74, listed below in table 1, wherein $R^1$, $R^6$ and $R^7$ have the meanings given in table 1:

TABLE 1

I.1

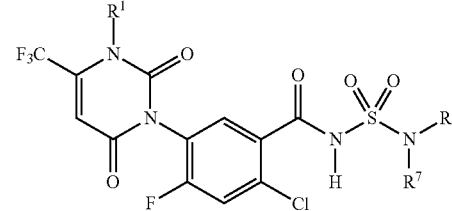

| 3-phenyluracil | $R^1$ | $R^6$ | $R^7$ |
|---|---|---|---|
| I.1.1 | methyl | methyl | methyl |
| I.1.2 | amino | methyl | methyl |
| I.1.3 | methyl | methyl | ethyl |
| I.1.4 | amino | methyl | ethyl |
| I.1.5 | methyl | methyl | propyl |
| I.1.6 | amino | methyl | propyl |
| I.1.7 | methyl | methyl | isopropyl |
| I.1.8 | amino | methyl | isopropyl |
| I.1.9 | methyl | methyl | butyl |
| I.1.10 | amino | methyl | butyl |
| I.1.11 | methyl | methyl | s-butyl |
| I.1.12 | amino | methyl | s-butyl |
| I.1.13 | methyl | methyl | isobutyl |
| I.1.14 | amino | methyl | isobutyl |
| I.1.15 | methyl | methyl | t-butyl |
| I.1.16 | amino | methyl | t-butyl |
| I.1.17 | methyl | methyl | n-pentyl |
| I.1.18 | amino | methyl | n-pentyl |
| I.1.19 | methyl | methyl | n-hexyl |
| I.1.20 | amino | methyl | n-hexyl |
| I.1.21 | methyl | methyl | allyl |
| I.1.22 | amino | methyl | allyl |
| I.1.23 | methyl | methyl | propargyl |
| I.1.24 | amino | methyl | propargyl |
| I.1.25 | methyl | methyl | phenyl |
| I.1.26 | amino | methyl | phenyl |
| I.1.27 | methyl | methyl | benzyl |
| I.1.28 | amino | methyl | benzyl |

TABLE 1-continued

I.1

[Structure: 3-phenyluracil with R¹ on N, F₃C group, connected to phenyl ring with F and Cl substituents, and a benzamide with sulfonamide group having R⁶ and R⁷ substituents]

| 3-phenyluracil | R¹ | R⁶ | R⁷ |
|---|---|---|---|
| I.1.29 | methyl | ethyl | ethyl |
| I.1.30 | amino | ethyl | ethyl |
| I.1.31 | methyl | ethyl | propyl |
| I.1.32 | amino | ethyl | propyl |
| I.1.33 | methyl | ethyl | isopropyl |
| I.1.34 | amino | ethyl | isopropyl |
| I.1.35 | methyl | ethyl | butyl |
| I.1.36 | amino | ethyl | butyl |
| I.1.37 | methyl | ethyl | n-pentyl |
| I.1.38 | amino | ethyl | n-pentyl |
| I.1.39 | methyl | ethyl | n-hexyl |
| I.1.40 | amino | ethyl | n-hexyl |
| I.1.41 | methyl | propyl | propyl |
| I.1.42 | amino | propyl | propyl |
| I.1.43 | methyl | propyl | isopropyl |
| I.1.44 | amino | propyl | isopropyl |
| I.1.45 | methyl | propyl | butyl |
| I.1.46 | amino | propyl | butyl |
| I.1.47 | methyl | propyl | n-pentyl |
| I.1.48 | amino | propyl | n-pentyl |
| I.1.49 | methyl | propyl | n-hexyl |
| I.1.50 | amino | propyl | n-hexyl |
| I.1.51 | methyl | isopropyl | isopropyl |
| I.1.52 | amino | isopropyl | isopropyl |
| I.1.53 | methyl | isopropyl | butyl |
| I.1.54 | amino | isopropyl | butyl |
| I.1.55 | methyl | isopropyl | n-pentyl |
| I.1.56 | amino | isopropyl | n-pentyl |
| I.1.57 | methyl | isopropyl | n-hexyl |
| I.1.58 | amino | isopropyl | n-hexyl |
| I.1.59 | methyl | butyl | butyl |
| I.1.60 | amino | butyl | butyl |
| I.1.61 | methyl | butyl | n-pentyl |
| I.1.62 | amino | butyl | n-pentyl |
| I.1.63 | methyl | butyl | n-hexyl |
| I.1.64 | amino | butyl | n-hexyl |
| I.1.65 | methyl | n-pentyl | n-pentyl |
| I.1.66 | amino | n-pentyl | n-pentyl |
| I.1.67 | methyl | n-pentyl | n-hexyl |
| I.1.68 | amino | n-pentyl | n-hexyl |
| I.1.69 | methyl | n-hexyl | n-hexyl |
| I.1.70 | amino | n-hexyl | n-hexyl |
| I.1.71 | methyl | —(CH₂)₄— | |
| I.1.72 | amino | —(CH₂)₄— | |
| I.1.73 | methyl | —(CH₂)₂—O—(CH₂)₂— | |
| I.1.74 | amino | —(CH₂)₂—O—(CH₂)₂— | |

In an especially preferred embodiment of the invention, the compositions comprise 3-phenyluracil I.1.7.

Among those compositions according to the present invention, preference is given to those which comprise at least one herbicide III selected from groups III.1 to III.7, III.9 to III.11, III.13, III.14 and III.15; preferably in combination with a 3-phenyluracil Ia or Ib.

Among those compositions according to the present invention, preference is given to those which comprise at least one herbicide III selected from groups III.1, III.2, III.3, III.5, III.6, III.7, III.9, III.10, III.13, III.14 and III.15; in particular selected from groups III.1, III.2, III.3, III.5, III.13 and III.15; preferably in combination with a 3-phenyluracil Ia or Ib.

Preferred herbicides of groups III.1) to III.15) are the compounds listed below:

III.1) from the group of the lipid biosynthesis inhibitors:
chlorazifop, clodinafop, clofop, cyhalofop, diclofop, fenoxaprop, fenoxaprop-p, fenthiaprop, fluazifop, fluazifop-P, haloxyfop, haloxyfop-P, isoxapyrifop, metamifop, propaquizafop, quizalofop, quizalofop-P, trifop, alloxydim, butroxydim, clethodim, cloproxydim, cycloxydim, profoxydim, sethoxydim, tepraloxydim, tralkoxydim, butylate, cycloate, diallate, dimepiperate, EPTC, esprocarb, ethiolate, isopolinate, methiobencarb, molinate, orbencarb, pebulate, prosulfocarb, sulfallate, thiobencarb, tiocarbazil, triallate, vernolate, benfuresate, ethofumesate, bensulide and pinoxaden;

III.2) from the group of the ALS inhibitors:
amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid, pyrithiobac, flucetosulfuron, orthosulfamuron, pyrimisulfan and [N-(5,7-dimethoxy [1,2,4]triazolo[1,5-α]pyrimidin-2-yl-2-methoxy-4-(trifluormethyl)-3-pyridinesulfonamide, known from WO 02/36595;

especially preferred amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid, pyrithiobac, flucetosulfuron, orthosulfamuron and pyrimisulfan;

III.3) from the group of the photosynthesis inhibitors:
atraton, atrazine, ametryne, aziprotryne, cyanazine, cyanatryn, chlorazine, cyprazine, desmetryne, dimethametryne, dipropetryn, eglinazine, ipazine, mesoprazine, methometon, methoprotryne, procyazine, proglinazine, prometon, prometryne, propazine, sebuthylazine, secbumeton, simazine, simeton, simetryne, terbumeton, terbuthylazine, terbutryne, trietazine, ametridione, amibuzin, hexazinone, isomethiozin, metamitron, metribuzin, bromacil, isocil, lenacil, terbacil, brompyrazon, chloridazon, dimidazon, desmedipham, phenisopham, phenmedipham, phenmedipham-ethyl, benzthiazuron, buthiuron, ethidimuron, isouron, methabenzthiazuron, monoisouron, tebuthiuron, thiazafluoron, anisuron, buturon, chlorbromuron, chloreturon, chlorotoluron, chloroxuron, difenoxuron, dimefuron, diuron, fenuron, fluometuron, fluothiuron, isoproturon, linuron, methiuron, metobenzuron, metobromuron, metoxuron, monolinuron, monuron, neburon, parafluoron, phenobenzuron, siduron, tetrafluoron, thidiazuron, cyperquat, diethamquat, difenzoquat, diquat, morfamquat, paraquat, bromobonil, bromoxynil, chloroxynil, iodobonil, ioxynil, amicarbazone, bromofenoxim, flumezin, methazole, bentazone, propanil, pentanochlor, pyridate, and pyridafol;

III.4) from the group of the protoporphyrinogen-IX oxidase inhibitors:

acifluorfen, bifenox, chlomethoxyfen, chlornitrofen, ethoxyfen, fluorodifen, fluoroglycofen, fluoronitrofen, fomesafen, furyloxyfen, halosafen, lactofen, nitrofen, nitrofluorfen, oxyfluorfen, fluazolate, pyraflufen, cinidon-ethyl, flumiclorac, flumioxazin, flumipropyn, fluthiacet, thidiazimin, oxadiazon, oxadiargyl, azafenidin, carfentrazone, sulfentrazone, pentoxazone, benzfendizone, butafenacil, pyraclonil, profluazol, flufenpyr, flupropacil, nipyraclofen, etnipromid, bencarbazone and 3-{2-chloro-4-fluoro-5-[3-methyl-2,6-dioxo-4-(trifluoromethyl)-1,2,3,6-tetrahydropyrimidin-1-yl]phenoxy}-2-(ethoxycarbonyl)methoxypyridine (known from WO 06/61562); especially preferred acifluorfen, bifenox, chlomethoxyfen, chlornitrofen, ethoxyfen, fluorodifen, fluoroglycofen, fluoronitrofen, fomesafen, furyloxyfen, halosafen, lactofen, nitrofen, nitrofluorfen, oxyfluorfen, fluazolate, pyraflufen, cinidon-ethyl, flumiclorac, flumioxazin, flumipropyn, fluthiacet, thidiazimin, oxadiazon, oxadiargyl, azafenidin, carfentrazone, sulfentrazone, pentoxazone, benzfendizone, butafenacil, pyraclonil, profluazol, flufenpyr, flupropacil, nipyraclofen, etnipromid, and bencarbazone;

III.5) from the group of the bleacher herbicides:

metflurazon, norflurazon, flufenican, diflufenican, picolinafen, beflubutamid, fluridone, fluorochloridone, flurtamone, mesotrione, sulcotrione, isoxachlortole, isoxaflutole, benzofenap, pyrazolynate, pyrazoxyfen, benzobicyclon, amitrole, clomazone, aclonifen, 4-(3-trifluoromethyl-phenoxy)-2-(4-trifluoromethylphenyl)pyrimidine, known from EP 723960, topramezone, 4-hydroxy-3-{[2-methyl-6-(trifluoromethyl)-3-pyridinyl]carbonyl}bicyclo[3.2.1]oct-3-en-2-one, known from WO 00/15615, 4-hydroxy-3-{[2-(2-methoxyethoxy)methyl-6-(trifluoro-methyl)-3-pyridinyl]carbonyl}bicylo[3.2.1]oct-3-en-2-one, known from WO 01/94339, 4-hydroxy-3-[4-(methylsulfonyl)-2-nitrobenzoyl]bicyclo[3.2.1]-oct-3-en-2-one, known from EP 338992, 2-[2-chloro-4-(methylsulfonyl)-3-[(2,2,2-trifluoroethoxy)methyl]benzoyl]-3-hydroxy-2-cyclohexen-1-one (known from DE 19846792), and pyrasulfotole;

III.6) from the group of the EPSP synthase inhibitors: glyphosate;

III.7) from the group of the glutamine synthase inhibitors: glufosinate and bilanaphos;

III.8) from the group of the DHP synthase inhibitors: asulam;

III.9) from the group of the mitose inhibitors:

benfluralin, butralin, dinitramine, ethalfluralin, fluchloralin, isopropalin, methalpropalin, nitralin, oryzalin, pendimethalin, prodiamine, profluralin, trifluralin, amiprofos-methyl, butamifos, dithiopyr, thiazopyr, propyzamide, tebutam, chlorthal, carbetamide, chlorbufam, chlorpropham and propham;

III.10) from the group of the VLCFA inhibitors:

acetochlor, alachlor, butachlor, butenachlor, delachlor, diethatyl, dimethachlor, dimethenamid, dimethenamid-P, metazachlor, metolachlor, S-metolachlor, pretilachlor, propachlor, propisochlor, prynachlor, terbuchlor, thenylchlor, xylachlor, allidochlor, CDEA, epronaz, diphenamid, napropamide, naproanilide, pethoxamid, flufenacet, mefenacet, fentrazamide, anilofos, piperophos, cafenstrole, indanofan and tridiphane;

III.11) from the group of the cellulose biosynthesis inhibitors:

dichlobenil, chlorthiamid, isoxaben and flupoxam;

III.12) from the group of the decoupler herbicides:

dinofenate, dinoprop, dinosam, dinoseb, dinoterb, DNOC, etinofen and medinoterb;

III.13) from the group of the auxin herbicides:

clomeprop, 2,4-D, 2,4,5-T, MCPA, MCPA thioethyl, dichlorprop, dichlorprop-P, mecoprop, mecoprop-P, 2,4-DB, MCPB, chloramben, dicamba, 2,3,6-TBA, tricamba, quinclorac, quinmerac, clopyralid, fluoroxypyr, picloram, triclopyr, benazolin and aminopyralid;

III.14) from the group of the auxin transport inhibitors:

naptalam, diflufenzopyr;

III.15) benzoylprop, flamprop, flamprop-M, bromobutide, chlorflurenol, cinmethylin, methyldymron, etobenzanid, fosamine, metam, pyributicarb, oxaziclomefone, dazomet, triaziflam, methyl bromide;

and the agriculturally acceptable salts and the agriculturally acceptable derivatives of these herbicides, provided they have a carboxyl group.

Particularly preferred herbicides of groups III.1) to III.15) are the compounds listed below:

III.1) from the group of the lipid biosynthesis inhibitors:

clodinafop, cyhalofop, diclofop, fenoxaprop, fenoxaprop-p, fluazifop, fluazifop-P, haloxyfop, haloxyfop-P, metamifop, quizalofop, quizalofop-P, alloxydim, butroxydim, clethodim, cloproxydim, cycloxydim, profoxydim, sethoxydim, tepraloxydim, tralkoxydim and pinoxaden;

III.2) from the group of the ALS inhibitors:

amidosulfuron, bensulfuron, chlorimuron, chlorsulfuron, cyclosulfamuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid, pyrithiobac, flucetosulfuron, orthosulfamuron, pyrimisulfan and [N-(5,7-dimethoxy[1,2,4]triazolo[1,5-α]pyrimidin-2-yl-2-methoxy-4-(trifluormethyl)-3-pyridinesulfonamide;

especially preferred amidosulfuron, bensulfuron, chlorimuron, chlorsulfuron, cyclosulfamuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid, pyrithiobac, flucetosulfuron, orthosulfamuron and pyrimisulfan;

III.3) from the group of the photosynthesis inhibitors:

atrazine, cyanazine, simazine, terbuthylazine, metamitron, metribuzin, chloridazon, amicarbazone, chlorotoluron, diuron, isoproturon, methabenzthiazuron, bentazone, propanil, bromoxynil, ioxynil and paraquat;

III.5) from the group of the bleacher herbicides:
norflurazon, diflufenican, picolinafen, beflubutamid, mesotrione, sulcotrione, isoxaflutole, benzofenap, pyrazolynate, pyrazoxyfen, benzobicyclon, 4-(3-trifluoromethylphenoxy)-2-(4-trifluoromethylphenyl)pyrimidine, topramezone, 4-hydroxy-3-{[2-methyl-6-(trifluoromethyl)-3-pyridinyl]carbonyl}bicyclo[3.2.1]oct-3-en-2-one, 4-hydroxy-3-{[2-(2-methoxyethoxy) methyl-6-(trifluoro-methyl)-3-pyridinyl] carbonyl}bicylo[3.2.1]oct-3-en-2-one, 4-hydroxy-3-[4-(methylsulfonyl)-2-nitrobenzoyl]bicyclo[3.2.1]-oct-3-en-2-one, 2-[2-chloro-4-(methylsulfonyl)-3-[(2,2,2-trifluoroethoxy)methyl]benzoyl]-3-hydroxy-2-cyclohexen-1-one and pyrasulfotole;

III.6) from the group of the EPSP synthase inhibitors:
glyphosate;

III.7) from the group of the glutamine synthase inhibitors:
glufosinate;

III.9) from the group of the mitose inhibitors:
oryzalin, pendimethalin and trifluralin;

III.10) from the group of the VLCFA inhibitors:
acetochlor, butachlor, dimethenamid, dimethenamid-P, metazachlor, metolachlor, S-metolachlor, pethoxamid, pretilachlor, flufenacet, mefenacet, fentrazamide, cafenstrole and indanofan;

III.13) from the group of the auxin herbicides:
2,4-D, dichlorprop, dichlorprop-P, mecoprop, MCPA, mecoprop-P, dicamba, quinclorac, quinmerac, clopyralid, fluoroxypyr, picloram, triclopyr and aminopyralid;

III.14) from the group of the auxin transport inhibitors:
diflufenzopyr;

III.15) cinmethylin, oxaziclomefone and triaziflam;

and the agriculturally acceptable salts and the agriculturally acceptable derivatives of these herbicides, provided they have a carboxyl group.

The categorization of the herbicides III according to their mode of action is based on current understanding. If a herbicide acts by more than one mode of action, this substance was assigned to only one mode of action.

Particular preference is given to those binary and ternary compositions which comprise at least one 3-phenyluracil I and N-[[4-[(cyclopropylamino)carbonyl]phenyl]sulfonyl]-2-methoxybenzamide II and, if appropriate, one or more herbicides III.

Here and below, the term "binary compositions" includes compositions which comprise one or more (for example 2 or 3) 3-phenyluracils I and N-[[4-[(cyclopropylamino)-carbonyl]phenyl]sulfonyl]-2-methoxybenzamide II.

Correspondingly, the term "ternary compositions" includes compositions which comprise one or more (for example 2 or 3) 3-phenyluracils I, N-[[4-[(cyclopropylamino)-carbonyl]phenyl]sulfonyl]-2-methoxybenzamide II, and one or more (for example 2 or 3) herbicides III.

In binary compositions the weight ratio of the active compounds I: II is usually in the range from 1:10 to 10:1, preferably in the range from 1:5 to 5:1, in particular in the range from 1:3 to 3:1.

In ternary compositions which comprise both a 3-phenyluracil I, N-[[4-[(cyclopropyl-amino)carbonyl]phenyl]sulfonyl]-2-methoxybenzamide II and at least one herbicide III, the relative weight ratios of the components I: II: III are usually in the range from 10:1:1 to 1:10:20, preferably from 5:1:1 to 1:5:10, in particular from 3:1:1 to 1:3:5.

In these ternary compositions, the weight ratio of N-[[4-[(cyclopropylamino)carbonyl]-phenyl]sulfonyl]-2-methoxybenzamide II to herbicide III is preferably in the range from 10:1 to 1:20.

In a particularly preferred embodiment of the invention, preference is given to those compositions of the invention which comprise a 3-phenyluracil I, especially Ia or Ib, in combination with N-[[4-[(cyclopropylamino)carbonyl]phenyl]sulfonyl]-2-methoxy-benzamide II.

Preference is also given to those compositions of the invention comprising as the only herbicidal active compound a 3-phenyluracil I,
preferably phenyluracil Ia or Ib,
particularly preferred phenyluracil I selected from the group consisting of 3-phenyluracils I.1.1 to 1.1.74,
especially preferred 3-phenyluracil I.1.7,
in combination with the safener N-[[4-[(cyclopropylamino)carbonyl]phenyl]sulfonyl]-2-methoxybenzamide II.

Preference is also given to those compositions of the invention comprising as the only herbicidal active compound phenyluracil Ia in combination with the safener N-[[4-[(cyclopropylamino)carbonyl]phenyl]sulfonyl]-2-methoxybenzamide II.

Furthermore preference is given to those compositions of the invention comprising a 3-phenyluracil I,
preferably phenyluracil Ia or Ib,
particularly preferred phenyluracil I selected from the group consisting of 3-phenyluracils I.1.1 to 1.1.74,
especially preferred 3-phenyluracil I.1.7,
in combination with N-[[4-[(cyclopropylamino)carbonyl]phenyl]sulfonyl]-2-methoxybenzamide II, and
at least one, especially exactly one, herbicide III selected from the classes III.1) to III.15).

Preference is also given to those compositions of the invention comprising 3-phenyluracil Ia, in combination with N-[[4-[(cyclopropylamino)carbonyl]phenyl]sulfonyl]-2-methoxybenzamide II and at least one, especially exactly one, herbicide III selected from the classes III.1) to III.15).

In another particularly preferred embodiment of the invention, preference is given to those compositions of the invention which comprise a 3-phenyluracil I, especially Ia or Ib, preferably phenyluracil Ia, particularly preferred phenyluracil I.1.7, in combination with N-[[4-[(cyclopropylamino)carbonyl]phenyl]sulfonyl]-2-methoxybenzamide II, and at least one, especially exactly one, herbicidally active compound of the group III.1), in particular selected from the group consisting of clodinafop, cyhalofop, diclofop, fenoxaprop, fenoxaprop-p, fluazifop, fluazifop-P, haloxyfop, haloxyfop-P, metamifop, quizalofop, quizalofop-P, alloxydim, butroxydim, clethodim, cloproxydim, cycloxydim, profoxydim, sethoxydim, tepraloxydim, tralkoxydim and pinoxaden.

In another particularly preferred embodiment of the invention, preference is given to those compositions of the invention which comprise a 3-phenyluracil I, especially Ia or Ib, preferably phenyluracil Ia, particularly preferred phenyluracil I.1.7, in combination with N-[[4-[(cyclopropylamino)carbonyl]phenyl]sulfonyl]-2-methoxybenzamide II, and at least one, especially exactly one, herbicidally active compound of the group III.2), in particular selected from the group consisting of amidosulfuron, bensulfuron, chlorimuron, chlorsulfuron, cyclosulfamuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid, pyrithiobac, flucetosulfuron, orthosulfamuron, pyrimisulfan and [N-(5,7-dimethoxy[1,2,4]triazolo[1,5-α]pyrimidin-2-yl-2-methoxy-4-(trifluormethyl)-3-pyridinesulfonamide.

In a further particularly preferred embodiment of the invention, preference is given to those compositions of the invention which comprise a 3-phenyluracil I, especially Ia or Ib, preferably phenyluracil Ia, particularly preferred phenyluracil I.1.7, in combination with N-[[4-[(cyclopropylamino)carbonyl]phenyl]sulfonyl]-2-methoxybenzamide II, and at least one, especially exactly one, herbicidally active compound of the group III.2), in particular selected from the group consisting of amidosulfuron, bensulfuron, chlorimuron, chlorsulfuron, cyclosulfamuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid, pyrithiobac, flucetosulfuron, orthosulfamuron and pyrimisulfan.

In another particularly preferred embodiment of the invention, preference is given to those compositions of the invention which comprise a 3-phenyluracil I, especially Ia or Ib, preferably phenyluracil Ia, particularly preferred phenyluracil I.1.7, in combination with N-[[4-[(cyclopropylamino)carbonyl]phenyl]sulfonyl]-2-methoxybenzamide II, and at least one, especially exactly one, herbicidally active compound of the group III.3), in particular selected from the group consisting of atrazine, cyanazine, simazine, terbuthylazine, metamitron, metribuzin, chloridazon, amicarbazone, chlorotoluron, diuron, isoproturon, methabenzthiazuron, bentazone, propanil, pyridate, bromoxynil, ioxynil and paraquat.

In another particularly preferred embodiment of the invention, preference is given to those compositions of the invention which comprise a 3-phenyluracil I, especially Ia or Ib, preferably phenyluracil Ia, particularly preferred phenyluracil I.1.7, in combination with N-[[4-[(cyclopropylamino)carbonyl]phenyl]sulfonyl]-2-methoxybenzamide II, and at least one, especially exactly one, herbicidally active compound of the group III.5), in particular selected from the group consisting of diflufenican, picolinafen, mesotrione, sulcotrione, isoxaflutole, benzofenap, pyrazolynate, pyrazoxyfen, benzobicyclon, 4-(3-trifluoromethylphenoxy)-2-(4-trifluoromethylphenyl)pyrimidine, topramezone, 4-hydroxy-3-{[2-methyl-6-(trifluoromethyl)-3-pyridinyl]carbonyl}bicyclo[3.2.1]oct-3-en-2-one, 4-hydroxy-3-{[2-(2-methoxyethoxy)methyl-6-(trifluoro-methyl)-3-pyridinyl]carbonyl}bicylo[3.2.1]oct-3-en-2-one, 4-hydroxy-3-[4-(methylsulfonyl)-2-nitrobenzoyl]bicyclo[3.2.1]-oct-3-en-2-one, 2-[2-chloro-4-(methylsulfonyl)-3-[(2,2,2-trifluoroethoxy)methyl]benzoyl]-3-hydroxy-2-cyclohexen-1-one and pyrasulfotole.

In another particularly preferred embodiment of the invention, preference is given to those compositions of the invention which comprise a 3-phenyluracil I, especially Ia or Ib, preferably phenyluracil Ia, particularly preferred phenyluracil I.1.7, in combination with N-[[4-[(cyclopropylamino)carbonyl]phenyl]sulfonyl]-2-methoxybenzamide II, and at least one, especially exactly one, herbicidally active compound of the group III.6), in particular glyphosate.

In another particularly preferred embodiment of the invention, preference is given to those compositions of the invention which comprise a 3-phenyluracil I, especially Ia or Ib, preferably phenyluracil Ia, particularly preferred phenyluracil I.1.7, in combination with N-[[4-[(cyclopropylamino)carbonyl]phenyl]sulfonyl]-2-methoxybenzamide II, and at least one, especially exactly one, herbicidally active compound of the group III.7), in particular glufosinate.

In another particularly preferred embodiment of the invention, preference is given to those compositions of the invention which comprise a 3-phenyluracil I, especially Ia or Ib, preferably phenyluracil Ia, particularly preferred phenyluracil I.1.7, in combination with N-[[4-[(cyclopropylamino)carbonyl]phenyl]sulfonyl]-2-methoxybenzamide II, and at least one, especially exactly one, herbicidally active compound of the group III.9), in particular oryzalin, pendimethalin and trifluralin.

In another particularly preferred embodiment of the invention, preference is given to those compositions of the invention which comprise a 3-phenyluracil I, especially Ia or Ib, preferably phenyluracil Ia, particularly preferred phenyluracil I.1.7, in combination with N-[[4-[(cyclopropylamino)carbonyl]phenyl]sulfonyl]-2-methoxybenzamide II, and at least one, especially exactly one, herbicidally active compound of the group III.10), in particular selected from the group consisting of acetochlor, butachlor, dimethenamid, dimethenamid-P, metazachlor, metolachlor, S-metolachlor, pethoxamid, pretilachlor, flufenacet, mefenacet, fentrazamide, cafenstrole and indanofan.

In another particularly preferred embodiment of the invention, preference is given to those compositions of the invention which comprise a 3-phenyluracil I, especially Ia or Ib, preferably phenyluracil Ia, particularly preferred phenyluracil I.1.7, in combination with N-[[4-[(cyclopropylamino)carbonyl]phenyl]sulfonyl]-2-methoxybenzamide II, and at least one, especially exactly one, herbicidally active compound of the group III.13), in particular selected from the group consisting of 2,4-D, dichlorprop, dichlorprop-P, mecoprop, MCPA, mecoprop-P, dicamba, quinclorac, quinmerac, clopyralid, fluoroxypyr, picloram, triclopyr and aminopyralid.

In another particularly preferred embodiment of the invention, preference is given to those compositions of the invention which comprise a 3-phenyluracil I, especially Ia or Ib, preferably phenyluracil Ia, particularly preferred phenyluracil I.1.7, in combination with N-[[4-[(cyclopropylamino)carbonyl]phenyl]sulfonyl]-2-methoxybenzamide II, and at least one, especially exactly one, herbicidally active compound of the group III.14), in particular diflufenzopyr.

In another particularly preferred embodiment of the invention, preference is given to those compositions of the invention which comprise a 3-phenyluracil I, especially Ia or Ib, preferably phenyluracil Ia, particularly preferred phenyluracil I.1.7, in combination with N-[[4-[(cyclopropylamino)carbonyl]phenyl]sulfonyl]-2-methoxybenzamide II, and at least one, especially exactly one, herbicidally active compound of the group III.15), in particular selected from the group consisting of cinmethylin, oxaziclomefone and triaziflam.

In the preferred or especially preferred compositions described above the 3-phenyl-uracils 1, N-[[4-[(cyclopropylamino)carbonyl]phenyl]sulfonyl]-2-methoxybenzamide II, and the herbicides III can be used in the form of their agriculturally acceptable salts or in the form of an agriculturally acceptable derivative thereof as described above.

The weight ratios of the individual components in the compositions are within the limits stated above.

Among the especially preferred compositions, particular preference is given to those compositions of the invention wherein the variables $R^1$ to $R^7$ have the preferred meanings, especially the particularly preferred meanings. Particular preference is given to 3-phenyluracils Ia and Ib, very particular to 3-phenyluracils I.1.1 to 1.1.74, as defined above.

Also particular preference is given to 3-phenyluracils Ia, especially to 3-phenyluracil I.1.7, as defined above.

Preference is also given, for example, to those compositions which comprise, as active compound I, the phenyluracil I.1.1 and, as further active compound, the safener N-[[4-[(cyclopropylamino)carbonyl]phenyl]sulfonyl]-2-methoxybenzamide II and, as further active compound, the substances listed in one row of table 2 (compositions 1.1 to 1.173).

The weight ratios of the individual components in the compositions 1.1 to 1.173 are within the stated limits, in the case of binary compositions of phenyluracil I.1.1 and N-[[4-[(cyclopropylamino)carbonyl]phenyl]sulfonyl]-2-methoxybenzamide II for example 1:1, and in the case of ternary compositions of phenyluracil I.1.1, N-[[4[(cyclopropylamino)carbonyl]phenyl]sulfonyl]-2-methoxybenzamide II and herbicide III for example 1:1:1, 2:1:1, 1:2:1, 1:5:1 or 1:5:2.

TABLE 2

| composition no. | herbicide III |
|---|---|
| 1.1 | clodinafop |
| 1.2 | cyhalofop |
| 1.3 | diclofop |
| 1.4 | fenoxaprop |
| 1.5 | fenoxaprop-P |
| 1.6 | fluazifop |
| 1.7 | fluazifop-P |
| 1.8 | haloxyfop |
| 1.9 | haloxyfop-P |
| 1.10 | metamifop |
| 1.11 | quizalofop |
| 1.12 | quizalofop-P |
| 1.13 | alloxydim |
| 1.14 | butroxydim |
| 1.15 | clethodim |
| 1.16 | cloproxydim |
| 1.17 | cycloxydim |
| 1.18 | profoxydim |
| 1.19 | sethoxydim |
| 1.20 | tepraloxydim |
| 1.21 | tralkoxydim |
| 1.22 | pinoxaden |
| 1.23 | amidosulfuron |
| 1.24 | azimsulfuron |
| 1.25 | bensulfuron |
| 1.26 | chlorimuron |
| 1.27 | chlorsulfuron |
| 1.28 | cinosulfuron |
| 1.29 | cyclosulfamuron |
| 1.30 | ethametsulfuron |
| 1.31 | ethoxysulfuron |
| 1.32 | flazasulfuron |
| 1.33 | flupyrsulfuron |
| 1.34 | foramsulfuron |
| 1.35 | halosulfuron |
| 1.36 | imazosulfuron |
| 1.37 | iodosulfuron |
| 1.38 | mesosulfuron |
| 1.39 | metsulfuron |
| 1.40 | nicosulfuron |
| 1.41 | oxasulfuron |
| 1.42 | primisulfuron |

TABLE 2-continued

| composition no. | herbicide III |
|---|---|
| 1.43 | prosulfuron |
| 1.44 | pyrazosulfuron |
| 1.45 | rimsulfuron |
| 1.46 | sulfometuron |
| 1.47 | sulfosulfuron |
| 1.48 | thifensulfuron |
| 1.49 | triasulfuron |
| 1.50 | tribenuron |
| 1.51 | trifloxysulfuron |
| 1.52 | triflusulfuron |
| 1.53 | tritosulfuron |
| 1.54 | imazamethabenz |
| 1.55 | imazamox |
| 1.56 | imazapic |
| 1.57 | imazapyr |
| 1.58 | imazaquin |
| 1.59 | imazethapyr |
| 1.60 | cloransulam |
| 1.61 | diclosulam |
| 1.62 | florasulam |
| 1.63 | flumetsulam |
| 1.64 | metosulam |
| 1.65 | penoxsulam |
| 1.66 | bispyribac |
| 1.67 | pyriminobac |
| 1.68 | propoxycarbazone |
| 1.69 | flucarbazone |
| 1.70 | pyribenzoxim |
| 1.71 | pyriftalid |
| 1.72 | pyrithiobac |
| 1.73 | flucetosulfuron |
| 1.74 | orthosulfamuron |
| 1.75 | pyrimisulfan |
| 1.76 | [N-(5,7-dimethoxy[1,2,4]triazolo[1,5-α]pyrimidin-2-yl-2-methoxy-4-(trifluormethyl)-3-pyridinesulfonamide |
| 1.77 | atrazine |
| 1.78 | cyanazine |
| 1.79 | simazine |
| 1.80 | terbuthylazine |
| 1.81 | metamitron |
| 1.82 | metribuzin |
| 1.83 | amicarbazone |
| 1.84 | chloridazon |
| 1.85 | chlorotoluron |
| 1.86 | diuron |
| 1.87 | isoproturon |
| 1.88 | methabenzthiazuron |
| 1.89 | propanil |
| 1.90 | bromoxynil |
| 1.91 | ioxynil |
| 1.92 | bentazone |
| 1.93 | pyridate |
| 1.94 | paraquat |
| 1.95 | acifluorfen |
| 1.96 | fluoroglycofen |
| 1.97 | halosafen |
| 1.98 | lactofen |
| 1.99 | oxyfluorfen |
| 1.100 | fluazolate |
| 1.101 | pyraflufen |
| 1.102 | cinidon-ethyl |
| 1.103 | flumiclorac |
| 1.104 | flumioxazin |
| 1.105 | fluthiacet |
| 1.106 | oxadiazon |
| 1.107 | oxadiargyl |
| 1.108 | azafenidin |
| 1.109 | carfentrazone |
| 1.110 | sulfentrazone |
| 1.111 | pentoxazone |
| 1.112 | benzfendizone |
| 1.113 | butafenacil |
| 1.114 | pyraclonil |
| 1.115 | profluazol |
| 1.116 | flufenpyr |
| 1.117 | nipyraclofen |
| 1.118 | bencarbazone |

TABLE 2-continued

| composition no. | herbicide III |
|---|---|
| 1.119 | norflurazon |
| 1.120 | diflufenican |
| 1.121 | picolinafen |
| 1.122 | beflubutamid |
| 1.123 | mesotrione |
| 1.124 | sulcotrione |
| 1.125 | isoxaflutole |
| 1.126 | benzofenap |
| 1.127 | pyrazolynate |
| 1.128 | pyrazoxyfen |
| 1.129 | benzobicyclon |
| 1.130 | 4-(3-trifluoromethylphenoxy)-2-(4-trifluoromethylphenyl)pyrimidine |
| 1.131 | topramezone |
| 1.132 | 4-hydroxy-3-{[2-methyl-6-(trifluoromethyl)-3-pyridinyl]carbonyl}bicyclo[3.2.1]oct-3-en-2-one |
| 1.133 | 4-hydroxy-3-{[2-(2-methoxyethoxy)methyl-6-(trifluoro-methyl)-3-pyridinyl]carbonyl}bicylo[3.2.1]oct-3-en-2-one |
| 1.134 | 4-hydroxy-3-[4-(methylsulfonyl)-2-nitrobenzoyl]bicyclo[3.2.1]-oct-3-en-2-one |
| 1.135 | 2-[2-chloro-4-(methylsulfonyl)-3-[(2,2,2-trifluoroethoxy)methyl]benzoyl]-3-hydroxy-2-cyclohexen-1-one |
| 1.136 | pyrasulfotole |
| 1.137 | glyphosate |
| 1.138 | glufosinate |
| 1.139 | oryzalin |
| 1.140 | pendimethalin |
| 1.141 | trifluralin |
| 1.142 | acetochlor |
| 1.143 | butachlor |
| 1.144 | dimethenamid |
| 1.145 | dimethenamid-P |
| 1.146 | metazachlor |
| 1.147 | metolachlor |
| 1.148 | S-metolachlor |
| 1.149 | pethoxamid |
| 1.150 | pretilachlor |
| 1.151 | flufenacet |
| 1.152 | mefenacet |
| 1.153 | fentrazamide |
| 1.154 | cafenstrole |
| 1.155 | indanofan |
| 1.156 | 2,4-D |
| 1.157 | dichlorprop |
| 1.158 | dichlorprop-P |
| 1.159 | MCPA |
| 1.160 | mecoprop |
| 1.161 | mecoprop-P |
| 1.162 | dicamba |
| 1.163 | quinclorac |
| 1.164 | quinmerac |
| 1.165 | clopyralid |
| 1.166 | fluroxypyr |
| 1.167 | picloram |
| 1.168 | triclopyr |
| 1.169 | aminopyralid |
| 1.170 | diflufenzopyr |
| 1.171 | cinmethylin |
| 1.172 | oxaziclomefone |
| 1.173 | triaziflam |

Preference is also given to the compositions 2.1-2.173, which differ from the corresponding compositions 1.1-1.173 only in that the phenyluracil I.1.1 is replaced by the phenyluracil I.1.2.

Preference is also given to the compositions 3.1-3.173, which differ from the corresponding compositions 1.1-1.173 only in that the phenyluracil I.1.1 is replaced by the phenyluracil I.1.3.

Preference is also given to the compositions 4.1-4.173, which differ from the corresponding compositions 1.1-1.173 only in that the phenyluracil I.1.1 is replaced by the phenyluracil I.1.4.

Preference is also given to the compositions 5.1-5.173, which differ from the corresponding compositions 1.1-1.173 only in that the phenyluracil I.1.1 is replaced by the phenyluracil I.1.5.

Preference is also given to the compositions 6.1-6.173, which differ from the corresponding compositions 1.1-1.173 only in that the phenyluracil I.1.1 is replaced by the phenyluracil I.1.6.

Preference is also given to the compositions 7.1-7.173, which differ from the corresponding compositions 1.1-1.173 only in that the phenyluracil I.1.1 is replaced by the phenyluracil I.1.7.

Preference is also given to the compositions 8.1-8.173, which differ from the corresponding compositions 1.1-1.173 only in that the phenyluracil I.1.1 is replaced by the phenyluracil I.1.8.

Preference is also given to the compositions 9.1-9.173, which differ from the corresponding compositions 1.1-1.173 only in that the phenyluracil I.1.1 is replaced by the phenyluracil I.1.9.

Preference is also given to the compositions 10.1-10.173, which differ from the corresponding compositions 1.1-1.173 only in that the phenyluracil I.1.1 is replaced by the phenyluracil I.1.10.

Preference is also given to the compositions 11.1-11.173, which differ from the corresponding compositions 1.1-1.173 only in that the phenyluracil I.1.1 is replaced by the phenyluracil I.1.11.

Preference is also given to the compositions 12.1-12.173, which differ from the corresponding compositions 1.1-1.173 only in that the phenyluracil I.1.1 is replaced by the phenyluracil I.1.12.

Preference is also given to the compositions 13.1-13.173, which differ from the corresponding compositions 1.1-1.173 only in that the phenyluracil I.1.1 is replaced by the phenyluracil I.1.13.

Preference is also given to the compositions 14.1-14.173, which differ from the corresponding compositions 1.1-1.173 only in that the phenyluracil I.1.1 is replaced by the phenyluracil I.1.14.

Preference is also given to the compositions 15.1-15.173, which differ from the corresponding compositions 1.1-1.173 only in that the phenyluracil I.1.1 is replaced by the phenyluracil I.1.15.

Preference is also given to the compositions 16.1-16.173, which differ from the corresponding compositions 1.1-1.173 only in that the phenyluracil I.1.1 is replaced by the phenyluracil I.1.16.

Preference is also given to the compositions 17.1-17.173, which differ from the corresponding compositions 1.1-1.173 only in that the phenyluracil I.1.1 is replaced by the phenyluracil I.1.17.

Preference is also given to the compositions 18.1-18.173, which differ from the corresponding compositions 1.1-1.173 only in that the phenyluracil I.1.1 is replaced by the phenyluracil I.1.18.

Preference is also given to the compositions 19.1-19.173, which differ from the corresponding compositions 1.1-1.173 only in that the phenyluracil I.1.1 is replaced by the phenyluracil I.1.19.

Preference is also given to the compositions 20.1-20.173, which differ from the corresponding compositions 1.1-1.173 only in that the phenyluracil I.1.1 is replaced by the phenyluracil I.1.20.

Preference is also given to the compositions 21.1-21.173, which differ from the corresponding compositions 1.1-1.173 only in that the phenyluracil I.1.1 is replaced by the phenyluracil I.1.21.

Preference is also given to the compositions 22.1-22.173, which differ from the corresponding compositions 1.1-1.173 only in that the phenyluracil I.1.1 is replaced by the phenyluracil I.1.22.

Preference is also given to the compositions 23.1-23.173, which differ from the corresponding compositions 1.1-1.173 only in that the phenyluracil I.1.1 is replaced by the phenyluracil I.1.23.

Preference is also given to the compositions 24.1-24.173, which differ from the corresponding compositions 1.1-1.173 only in that the phenyluracil I.1.1 is replaced by the phenyluracil I.1.24.

Preference is also given to the compositions 25.1-25.173, which differ from the corresponding compositions 1.1-1.173 only in that the phenyluracil I.1.1 is replaced by the phenyluracil I.1.25.

Preference is also given to the compositions 26.1-26.173, which differ from the corresponding compositions 1.1-1.173 only in that the phenyluracil I.1.1 is replaced by the phenyluracil I.1.26.

Preference is also given to the compositions 27.1-27.173, which differ from the corresponding compositions 1.1-1.173 only in that the phenyluracil I.1.1 is replaced by the phenyluracil I.1.27.

Preference is also given to the compositions 28.1-28.173, which differ from the corresponding compositions 1.1-1.173 only in that the phenyluracil I.1.1 is replaced by the phenyluracil I.1.28.

Preference is also given to the compositions 29.1-29.173, which differ from the corresponding compositions 1.1-1.173 only in that the phenyluracil I.1.1 is replaced by the phenyluracil I.1.29.

Preference is also given to the compositions 30.1-30.173, which differ from the corresponding compositions 1.1-1.173 only in that the phenyluracil I.1.1 is replaced by the phenyluracil I.1.30.

Preference is also given to the compositions 31.1-31.173, which differ from the corresponding compositions 1.1-1.173 only in that the phenyluracil I.1.1 is replaced by the phenyluracil I.1.31.

Preference is also given to the compositions 32.1-32.173, which differ from the corresponding compositions 1.1-1.173 only in that the phenyluracil I.1.1 is replaced by the phenyluracil I.1.32.

Preference is also given to the compositions 33.1-33.173, which differ from the corresponding compositions 1.1-1.173 only in that the phenyluracil I.1.1 is replaced by the phenyluracil I.1.33.

Preference is also given to the compositions 34.1-34.173, which differ from the corresponding compositions 1.1-1.173 only in that the phenyluracil I.1.1 is replaced by the phenyluracil I.1.34.

Preference is also given to the compositions 35.1-35.173, which differ from the corresponding compositions 1.1-1.173 only in that the phenyluracil I.1.1 is replaced by the phenyluracil I.1.35.

Preference is also given to the compositions 36.1-36.173, which differ from the corresponding compositions 1.1-1.173 only in that the phenyluracil I.1.1 is replaced by the phenyluracil I.1.36.

Preference is also given to the compositions 37.1-37.173, which differ from the corresponding compositions 1.1-1.173 only in that the phenyluracil I.1.1 is replaced by the phenyluracil I.1.37.

Preference is also given to the compositions 38.1-38.173, which differ from the corresponding compositions 1.1-1.173 only in that the phenyluracil I.1.1 is replaced by the phenyluracil I.1.38.

Preference is also given to the compositions 39.1-39.173, which differ from the corresponding compositions 1.1-1.173 only in that the phenyluracil I.1.1 is replaced by the phenyluracil I.1.39.

Preference is also given to the compositions 40.1-40.173, which differ from the corresponding compositions 1.1-1.173 only in that the phenyluracil I.1.1 is replaced by the phenyluracil I.1.40.

Preference is also given to the compositions 41.1-41.173, which differ from the corresponding compositions 1.1-1.173 only in that the phenyluracil I.1.1 is replaced by the phenyluracil I.1.41.

Preference is also given to the compositions 42.1-42.173, which differ from the corresponding compositions 1.1-1.173 only in that the phenyluracil I.1.1 is replaced by the phenyluracil I.1.42.

Preference is also given to the compositions 43.1-43.173, which differ from the corresponding compositions 1.1-1.173 only in that the phenyluracil I.1.1 is replaced by the phenyluracil I.1.43.

Preference is also given to the compositions 44.1-44.173, which differ from the corresponding compositions 1.1-1.173 only in that the phenyluracil I.1.1 is replaced by the phenyluracil I.1.44.

Preference is also given to the compositions 45.1-45.173, which differ from the corresponding compositions 1.1-1.173 only in that the phenyluracil I.1.1 is replaced by the phenyluracil I.1.45.

Preference is also given to the compositions 46.1-46.173, which differ from the corresponding compositions 1.1-1.173 only in that the phenyluracil I.1.1 is replaced by the phenyluracil I.1.46.

Preference is also given to the compositions 47.1-47.173, which differ from the corresponding compositions 1.1-1.173 only in that the phenyluracil I.1.1 is replaced by the phenyluracil I.1.47.

Preference is also given to the compositions 48.1-48.173, which differ from the corresponding compositions 1.1-1.173 only in that the phenyluracil I.1.1 is replaced by the phenyluracil I.1.48.

Preference is also given to the compositions 49.1-49.173, which differ from the corresponding compositions 1.1-1.173 only in that the phenyluracil I.1.1 is replaced by the phenyluracil I.1.49.

Preference is also given to the compositions 50.1-50.173, which differ from the corresponding compositions 1.1-1.173 only in that the phenyluracil I.1.1 is replaced by the phenyluracil I.1.50.

Preference is also given to the compositions 51.1-51.173, which differ from the corresponding compositions 1.1-1.173 only in that the phenyluracil I.1.1 is replaced by the phenyluracil I.1.51.

Preference is also given to the compositions 52.1-52.173, which differ from the corresponding compositions 1.1-1.173 only in that the phenyluracil I.1.1 is replaced by the phenyluracil I.1.52.

Preference is also given to the compositions 53.1-53.173, which differ from the corresponding compositions 1.1-1.173 only in that the phenyluracil I.1.1 is replaced by the phenyluracil I.1.53.

Preference is also given to the compositions 54.1-54.173, which differ from the corresponding compositions 1.1-1.173 only in that the phenyluracil I.1.1 is replaced by the phenyluracil I.1.54.

Preference is also given to the compositions 55.1-55.173, which differ from the corresponding compositions 1.1-1.173 only in that the phenyluracil I.1.1 is replaced by the phenyluracil I.1.55.

Preference is also given to the compositions 56.1-56.173, which differ from the corresponding compositions 1.1-1.173 only in that the phenyluracil I.1.1 is replaced by the phenyluracil I.1.56.

Preference is also given to the compositions 57.1-57.173, which differ from the corresponding compositions 1.1-1.173 only in that the phenyluracil I.1.1 is replaced by the phenyluracil I.1.57.

Preference is also given to the compositions 58.1-58.173, which differ from the corresponding compositions 1.1-1.173 only in that the phenyluracil I.1.1 is replaced by the phenyluracil I.1.58.

Preference is also given to the compositions 59.1-59.173, which differ from the corresponding compositions 1.1-1.173 only in that the phenyluracil I.1.1 is replaced by the phenyluracil I.1.59.

Preference is also given to the compositions 60.1-60.173, which differ from the corresponding compositions 1.1-1.173 only in that the phenyluracil I.1.1 is replaced by the phenyluracil I.1.60.

Preference is also given to the compositions 61.1-61.173, which differ from the corresponding compositions 1.1-1.173 only in that the phenyluracil I.1.1 is replaced by the phenyluracil I.1.61.

Preference is also given to the compositions 62.1-62.173, which differ from the corresponding compositions 1.1-1.173 only in that the phenyluracil I.1.1 is replaced by the phenyluracil I.1.62.

Preference is also given to the compositions 63.1-63.173, which differ from the corresponding compositions 1.1-1.173 only in that the phenyluracil I.1.1 is replaced by the phenyluracil I.1.63.

Preference is also given to the compositions 64.1-64.173, which differ from the corresponding compositions 1.1-1.173 only in that the phenyluracil I.1.1 is replaced by the phenyluracil I.1.64.

Preference is also given to the compositions 65.1-65.173, which differ from the corresponding compositions 1.1-1.173 only in that the phenyluracil I.1.1 is replaced by the phenyluracil I.1.65.

Preference is also given to the compositions 66.1-66.173, which differ from the corresponding compositions 1.1-1.173 only in that the phenyluracil I.1.1 is replaced by the phenyluracil I.1.66.

Preference is also given to the compositions 67.1-67.173, which differ from the corresponding compositions 1.1-1.173 only in that the phenyluracil I.1.1 is replaced by the phenyluracil I.1.67.

Preference is also given to the compositions 68.1-68.173, which differ from the corresponding compositions 1.1-1.173 only in that the phenyluracil I.1.1 is replaced by the phenyluracil I.1.68.

Preference is also given to the compositions 69.1-69.173, which differ from the corresponding compositions 1.1-1.173 only in that the phenyluracil I.1.1 is replaced by the phenyluracil I.1.69.

Preference is also given to the compositions 70.1-70.173, which differ from the corresponding compositions 1.1-1.173 only in that the phenyluracil I.1.1 is replaced by the phenyluracil I.1.70.

Preference is also given to the compositions 71.1-71.173, which differ from the corresponding compositions 1.1-1.173 only in that the phenyluracil I.1.1 is replaced by the phenyluracil I.1.71.

Preference is also given to the compositions 72.1-72.173, which differ from the corresponding compositions 1.1-1.173 only in that the phenyluracil I.1.1 is replaced by the phenyluracil I.1.72.

Preference is also given to the compositions 73.1-73.173, which differ from the corresponding compositions 1.1-1.173 only in that the phenyluracil I.1.1 is replaced by the phenyluracil I.1.73.

Preference is also given to the compositions 74.1-74.173, which differ from the corresponding compositions 1.1-1.173 only in that the phenyluracil I.1.1 is replaced by the phenyluracil I.1.74.

Preference is also given to those compositions, which comprise, as active compound, the substances listet in one row of table 1 (3-phenyluracil I.1.1-1.1.74), and, as further active compound, the safener N-[[4-[(cyclopropylamino)carbonyl]phenyl]sulfonyl]-2-methoxybenzamide II, and, as further active compound, 3-{2-chloro-4-fluoro-5-[3-methyl-2,6-dioxo-4-(trifluoromethyl)-1,2,3,6-tetrahydropyrimidin-1-yl]phenoxy}-2-(ethoxycarbonyl)methoxypyridine.

The weight ratios of the individual components in the compositions 1.1 to 74.173 are within the limits stated above, in the case of binary compositions of 3-phenyluracil I and N-[[4-[(cyclopropylamino)carbonyl]phenyl]sulfonyl]-2-methoxybenzamide II for example 1:1, 1:2 or 1:5, and in the case of ternary compositions of 3-phenyluracil I, N-[[4-[(cyclopropylamino)carbonyl]phenyl]sulfonyl]-2-methoxybenzamide II and herbicide III for example 1:1:1, 2:1:1, 1:2:1, 1:5:1 or 1:5:2.

In the ready-to-use preparations, i.e. in the compositions according to the invention in the form of crop protection products, the components I and II and optionally III, in suspended, emulsified or dissolved form, can be present formulated jointly or separately. The use forms depend entirely on the intended use.

The compositions according to the invention can be applied, for example, in the form of directly sprayable aqueous solutions, powders, suspensions, also highly-concentrated aqueous, oily or other suspensions or dispersions, emulsions, oil dispersions, pastes, dusts, materials for spreading or granules, by means of spraying, atomizing, dusting, broadcasting or watering. The use forms depend on the intended use; in any case, they should ensure the finest possible distribution of the active compounds.

Depending on the form in which the ready-to-use preparations are present in the compositions according to the invention, they comprise one or more liquid or solid carriers, if appropriate surfactants and if appropriate further auxiliaries which are customary for formulating crop protection products. The person skilled in the art is sufficiently familiar with the recipes for such formulations.

The ready-to-use preparations comprise the components I and II and optionally III and auxiliaries which are customary for formulating crop protection products, which auxiliaries may also comprise a liquid carrier.

Suitable inert additives with carrier function are essentially: mineral oil fractions of medium to high boiling point, such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the active compounds I, II or III, as such or dissolved in an oil or solvent, can be homogenized in water by means of wetting agent, tackifier, dispersant or emulsifier. Alternatively, it is possible to prepare concentrates consisting of active substance, wetting agent, tackifier, dispersant or emulsifier and, if desired, solvent or oil, and these concentrates are suitable for dilution with water.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, of alkyl- and alkylarylsulfonates, of alkyl sulfates, lauryl ether sulfates and fatty alcohol sulfates, and salts of sulfated hexa-, hepta- and octadecanols and of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ether or polyoxypropylene alkyl ether, lauryl alcohol polyglycol ether acetate, sorbitol esters, lignosulfite waste liquors or methylcellulose.

Powders, materials for spreading and dusts can be prepared by mixing or concomitant grinding of the active substances with a solid carrier.

Granules, e.g. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin such as cereal meal, tree bark meal, wood meal and nutshell meal, cellulose powders, or other solid carriers.

The concentrations of the active compounds in the ready-to-use preparations can be varied within wide ranges. In general, the formulations comprise from 0.001 to 98% by weight, preferably 0.01 to 95% by weight, of active ingredients. The active ingredients are employed in a purity of from 90% to 100%, preferably 95% to 100% (according to NMR spectrum).

The compounds according to the invention can, for example, be formulated as follows:

I 20 parts by weight of the active compound composition in question are dissolved in a composition composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100 000 parts by weight of water and finely distributing it therein gives an aqueous dispersion which comprises 0.02% by weight of the active ingredient.

II 20 parts by weight of the active compound composition in question are dissolved in a composition composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100 000 parts by weight of water and finely distributing it therein gives an aqueous dispersion which comprises 0.02% by weight of the active ingredient.

III 20 parts by weight of the active compound composition in question are dissolved in a composition composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100 000 parts by weight of water and finely distributing it therein gives an aqueous dispersion which comprises 0.02% by weight of the active ingredient.

IV 20 parts by weight of the active compound composition in question are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the composition is ground in a hammer mill. Finely distributing the composition in 20 000 parts by weight of water gives a spray composition which comprises 0.1% by weight of the active ingredient.

V 3 parts by weight of the active compound composition in question are mixed with 97 parts by weight of finely divided kaolin. This gives a dust which comprises 3% by weight of the active ingredient.

VI 20 parts by weight of the active compound composition in question are mixed intimately with 2 parts by weight of calcium dodecylbenzenesulfonate, 8 parts by weight of fatty alcohol polyglycol ether, 2 parts by weight of the sodium salt of a phenol-urea-formaldehyde condensate and 68 parts by weight of a paraffinic mineral oil. This gives a stable oily dispersion.

VII 1 part by weight of the active compound composition in question is dissolved in a composition composed of 70 parts by weight of cyclohexanone, 20 parts by weight of ethoxylated isooctylphenol and 10 parts by weight of ethoxylated castor oil. This gives a stable emulsion concentrate.

VIII 1 part by weight of the active compound composition in question is dissolved in a composition composed of 80 parts by weight of cyclohexanone and 20 parts by weight of Wettol® EM 31 (nonionic emulsifier based on ethoxylated castor oil). This gives a stable emulsion concentrate.

The components I and II and optionally III can be formulated jointly or separately.

The components I and II and optionally III can be applied jointly or separately, simultaneously or successively, before, during or after emergence of the plants.

If the active compounds I and II and optionally III are less well tolerated by certain crop plants, it is possible to use application methods in which the herbicidal compositions are sprayed with the aid of sprayers in such a way that the leaves of the sensitive crop plants are as far as possible unaffected, whereas the active compounds reach the leaves of the undesirable plants growing underneath or the uncovered soil surface (post-directed, lay-by).

The required application rate of the composition of the pure active compounds, i.e. of I and II and optionally III without formulation auxiliary, depends on the density of the undesired vegetation, on the development stage of the plants, on the climatic conditions of the location where the composition is used and on the application method. In general, the application rate of I and II and optionally III is from 0.001 to 3 kg/ha, preferably from 0.005 to 2 kg/ha and in particular from 0.01 to 1 kg/ha of active substance.

The required application rates of the 3-phenyluracils I and N-[[4-[(cyclopropylamino)-carbonyl]phenyl]sulfonyl]-2-methoxybenzamide II are generally in the range from 0.1 g/ha to 1 kg/ha and preferably in the range from 1 g/ha to 500 g/ha or from 5 g/ha to 500 g/ha of active substance.

The compositions are applied to the plants mainly by spraying, in particular foliar spraying. Application can be carried out by customary spraying techniques using, for example, water as carrier and spray liquor rates of from about 50 to 1000 l/ha (for example from 300 to 400 l/ha). Application of the herbicidal compositions by the low-volume and the ultra-low-volume method is possible, as is their application in the form of microgranules.

The compositions according to the present invention are suitable for controlling common harmful plants in useful plants, in particular in crops such as oat, barley, millet, corn, rice, wheat, sugar cane, cotton, oilseed rape, flax, lentil, sugar beet, tobacco, sunflowers and soybeans or in perennial crops.

Moreover, it may be useful to apply the compositions according to the invention jointly as a composition with other crop protection products, for example with pesticides or agents for controlling phytopathogenic fungi or bacteria. Also of interest is the miscibility with mineral salt solutions which are employed for treating nutritional and trace element deficiencies. Non-phytotoxic oils and oil concentrates may also be added.

The compositions according to the invention can also be used in crop plants which, by genetic engineering or by breeding, are resistant to one or more herbicides and/or fungicides and/or or to attack by insects.

Suitable are for example crop plants preferably corn, wheat, barley, sunflower, rice, canola, soybeans which are resistant to herbicidal EPSP synthase inhibitors, such as, for example, glyphosate, to herbicidal glutamine synthase inhibitors, such as, for example, glufosinate, to herbicidal protoporphyrinogen-IX oxidase inhibitors, such as, for example, butafenacil, or to herbicidal ALS inhibitors, such as, for example, imazamethabenz, imazamox, imazapic, imazapyr, imazaquin, imazethapyr, or crop plants which, owing to introduction of the gene for Bt toxin by genetic modification, are resistant to attack by certain insects.

Surprisingly, the compositions according to the invention which, in addition to the 3-phenyluracil I and optionally a herbicide III, comprise the safener N-[[4-[(cyclopropylamino)carbonyl]phenyl]sulfonyl]-2-methoxybenzamide II, are better tolerated by useful plants than the respective compositions comprising a 3-phenyluracil I and optionally a herbicide III without safener II.

The 3-phenyluracils of formula I can be prepared by the preparation processes disclosed in WO 01/83459. With respect to the preparation of individual compounds, reference is made to the examples of WO 01/83459. Compounds, which are not explicitly disclosed in this document, can be prepared in an analogous manner.

N-[[4-[(cyclopropylamino)carbonyl]phenyl]sulfonyl]-2-methoxybenzamide II can be prepared by the preparation processes disclosed by the earlier applications WO 99/16744 and WO 05/00797.

USE EXAMPLES

The effect of the herbicidal compositions according to the invention of components I and II and, if appropriate, III on the growth of undesirable plants compared to the herbicidally active compounds alone can be demonstrated by the following greenhouse experiments.

For the pre-emergence treatment, directly after sowing the active compounds, which had been suspended or emulsified in water, were applied by means of finely distributed nozzles. The containers were irrigated gently to promote germination and growth and subsequently covered with transparent plastic hoods until plant had rooted. This cover caused uniform germination of the tests plants, unless this was adversely affected by active compounds.

For the post-emergence treatment, the test plants were first grown to a height of 3 to 20 cm, depending on the plant habit, and only then treated. Here, the herbicidal compositions were suspended or emulsified in water as distribution medium and sprayed using finely distributing nozzles.

The respective component I was formulated as a 12% by weight strength emulsion concentrate, and component II as a 10% by weight suspension concentrate. Optionally components III can be used in their appropriate available formulation types.

The components I, II and optionally III were introduced to the spray liquid with the amount of solvent system used for applying the active compound.

The test period extended over 21 days. During this time, the plants were tended, and their response to the treatments with active compound was evaluated.

The evaluation for the damage caused by the chemical compositions was carried out using a scale from 0 to 100%, compared to the untreated control plants. Here, 0 means no damage and 100 means complete destruction of the plants.

A safener action is present if the damage to the crop plant caused by a mixture according to the present invention which contains N-[[4-[(cyclopropylamino)carbonyl]phenyl]sulfonyl]-2-methoxybenzamide is less than the damage caused when the phenyluracil I optionally in mixture with a herbicide III according to the present invention is used without N-[[4-[(cyclopropylamino)carbonyl]phenyl]sulfonyl]-2-methoxybenzamide.

The plants used in these greenhouse experiments belong to the following species:

| BAYER-Code | Common name |
| --- | --- |
| TRZAS | spring wheat |
| HORVW | winter barley |
| ZEAMX | corn |
| POLCO | wild buckwheat |
| CHEAL | lambsquaters |
| ABUTH | velvetleaf |
| AMARE | common amaranth |

Example 1

Herbicidal action of the post-emergence applied mixture of 3-phenyluracil I.1.7 and N-[[4-[(cyclopropylamino)carbonyl]phenyl]sulfonyl]-2-methoxybenzamide II against POLCO, CHEAL, ABUTH and AMARE and safener action with regard to TRZAS, HORVW and ZEAMX

| Application rate in g/ha | | Damage to crop plant | | | Herbicidal action against | | | |
|---|---|---|---|---|---|---|---|---|
| I.1.7 | II | TRZAS | HORVW | ZEAMX | POLCO | CHEAL | ABUTH | AMARE |
| 6.25 | — | 35 | 40 | 50 | 100 | 100 | 100 | 100 |
| 6.25 | 150 | 20 | 35 | 35 | 100 | 100 | 100 | 100 |
| 3.125 | — | 20 | 35 | 35 | 100 | 100 | 100 | 100 |
| 3.125 | 150 | 10 | 20 | 30 | 100 | 100 | 100 | 100 |

The safener N-[[4-[(cyclopropylamino)carbonyl]phenyl]sulfonyl]-2-methoxybenzamide II has not shown damaging effect on TRZAS, HORVW and ZEAMX and has not shown herbicidal activity on POLCO, CHEAL, ABUTH and AMARE at application rates of 150 g/ha applied post-emergence.

We claim:

1. A composition comprising 3-phenyluracils of formula I:

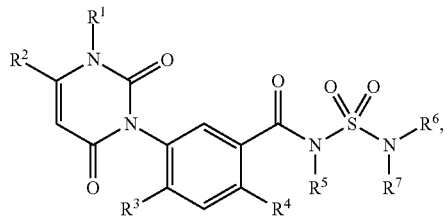

I wherein,
R$^1$ is methyl;
R$^2$ is CF$_3$;
R$^3$ is fluoro;
R$^4$ is chloro;
R$^5$ is hydrogen;
one of R$^6$ and R$^7$ is methyl and the other is isopropyl;
or agriculturally acceptable salts thereof; and
N-[[4-[(cyclopropylamino)carbonyl]phenyl]sulfonyl]-2-methoxybenzamide of formula II

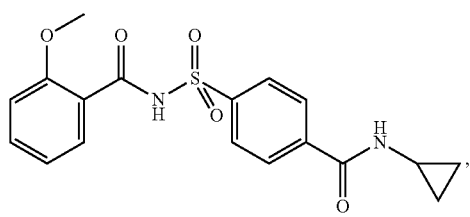

II or agriculturally acceptable salts thereof;
wherein the weight ratio of compound I to compound of formula II is 1:10 to 10:1.

2. The composition of claim 1 comprising as the only herbicidal active compound the 3-phenyluracil of formula I in combination with the safener N-[[4-[(cyclopropylamino)carbonyl]phenyl]sulfonyl]-2-methoxy benzamide of formula II.

3. The composition of claim 1 further comprising at least one inert liquid and/or solid carrier, optionally at least one or more surfactants and, optionally, at least one or more further auxiliaries.

4. A method for controlling undesired vegetation, which comprises applying a herbicidally effective amount of a composition comprising 3-phenyluracils of formula I:

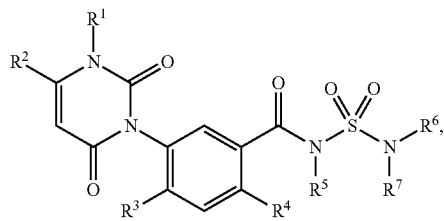

I wherein,
R$^1$ is methyl;
R$^2$ is CF$_3$;
R$^3$ is fluoro;
R$^4$ is chloro;
R$^5$ is hydrogen;
R$^6$, R$^7$ are methyl or isopropyl;
or agriculturally acceptable salts thereof;
compound of formula II

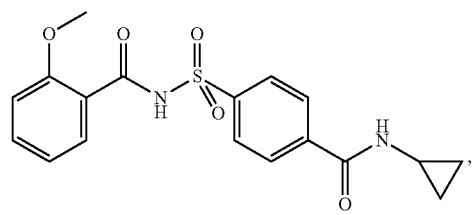

II or agriculturally acceptable salts thereof to plants, their habitat or seed;
and wherein the weight ratio of compound I to compound of formula II is 1:10 to 10:1.

5. A method for controlling undesired vegetation, which comprises applying compound of formula I:

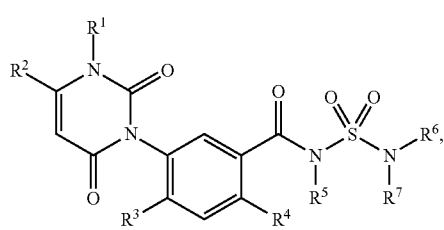

I and compound of formula II

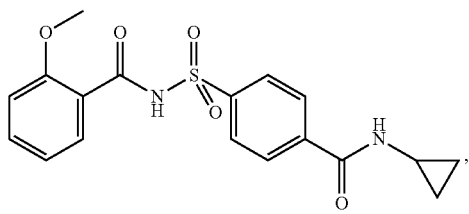

wherein the compounds or composition comprising the compounds are applied before, during and/or after the emergence of the undesirable plants, wherein components I and II are applied simultaneously or in succession;

wherein the weight ratio of compound I to compound of formula II is 1:10 to 10:1.

6. The method of claim 4, wherein the composition is applied for controlling undesirable vegetation in crop plants.

7. The method of claim 6 wherein the crop plant is selected from the group consisting of oat, barley, millet, corn, rice, wheat, sugar cane, cotton, oilseed rape, flax, lentil, sugar beet, tobacco, sunflowers and soybeans.

8. The method of claim 4, wherein the crop plant is a herbicide resistant and/or insect resistant and/or fungus resistant crop plant.

9. A method of safening the phytotoxic activity on crop plants comprising, applying a 3-phenyluracil of formula I

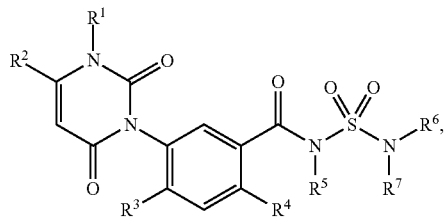

wherein, $R^1$ is methyl;

$R^2$ is $CF_3$;

$R^3$ is fluoro;

$R^4$ is chloro;

$R^5$ is hydrogen;

$R^6$, $R^7$ are methyl or isopropyl;

or an agriculturally acceptable salt thereof;

on crop plants, in combination with N-[[4-[(cyclopropylamino)carbonyl]-phenyl]sulfonyl]-2-methoxybenzamide of formula II

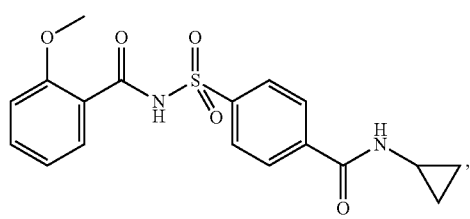

or an agriculturally acceptable salt thereof;

in an amount effective to reduce or eliminate phytotoxic activity of said 3-phenyluracil I;

and wherein the weight ratio of compound I to compound of formula II is 1:10 to 10:1.

10. The method of claim 9 wherein the crop plants are selected from the group consisting of oat, barley, millet, corn, rice, wheat, sugar cane, cotton, oilseed rape, flax, lentil, sugar beet, tobacco, sunflowers and soybeans.

11. The method of claim 9 which comprises applying as the only herbicidal active compound said 3-phenyluracil of formula I in combination with the safener N-[[4-[(cyclopropylamino)carbonyl]phenyl]sulfonyl]-2-methoxybenzamide of formula II.

* * * * *